US012616434B2

(12) United States Patent
Blecher

(10) Patent No.: US 12,616,434 B2
(45) Date of Patent: May 5, 2026

(54) SENSOR HOLDER AND METHOD FOR OPTIMUM POSITIONING DURING INTRAORAL IMAGING

(71) Applicant: DENTSPLY SIRONA Inc., York, PA (US)

(72) Inventor: Wolf Blecher, Hemsbach (DE)

(73) Assignee: Dentsply Sirona Inc., York, PA (US)

( * ) Notice: Subject to any disclaimer, the term of this patent is extended or adjusted under 35 U.S.C. 154(b) by 529 days.

(21) Appl. No.: 17/779,019

(22) PCT Filed: Nov. 27, 2020

(86) PCT No.: PCT/EP2020/083691
§ 371 (c)(1),
(2) Date: May 23, 2022

(87) PCT Pub. No.: WO2021/105397
PCT Pub. Date: Jun. 3, 2021

(65) Prior Publication Data
US 2023/0346326 A1 Nov. 2, 2023

(30) Foreign Application Priority Data
Nov. 28, 2019 (EP) .................................... 19212176

(51) Int. Cl.
| | |
|---|---|
| *A61B 6/51* | (2024.01) |
| *A61B 6/00* | (2006.01) |
| *A61B 6/58* | (2024.01) |

(52) U.S. Cl.
CPC ............ *A61B 6/512* (2024.01); *A61B 6/4435* (2013.01); *A61B 6/587* (2013.01)

(58) Field of Classification Search
CPC ........ A16B 6/512; A16B 6/4435; A16B 6/587
See application file for complete search history.

(56) References Cited

U.S. PATENT DOCUMENTS

| | | | |
|---|---|---|---|
| 4,598,416 A | 7/1986 | Donato | |
| 4,866,750 A | 9/1989 | Chavarria et al. | |

(Continued)

FOREIGN PATENT DOCUMENTS

| | | |
|---|---|---|
| CN | 101015444 | 8/2007 |
| CN | 103826566 | 5/2014 |

(Continued)

OTHER PUBLICATIONS

"European Application Serial No. 19212176.2, Extended European Search Report mailed Aug. 10, 2020", 13 pgs.

(Continued)

*Primary Examiner* — Lam S Nguyen
(74) *Attorney, Agent, or Firm* — SCHWEGMAN LUNDBERG & WOESSNER, P.A.

(57) ABSTRACT

A method for determining the optimum relative position of at least one sensor and/or at least one imaging source of an imaging device for at least one intraoral imaging, and for the non-overlapping imaging of at least two tooth root canals. The disclosure also relates to a sensor holder (1) for intraoral imaging including at least one biting device (2) that is insertable into the mouth of a patient, at least one holding device (3) at least indirectly engaged with the biting device (2) for fixing at least one sensor, and at least one centering device (4) for aligning at least one imaging device. The centering device (4) is at least indirectly in operative connection with the biting device (2) via at least one centering device holding portion (5).

9 Claims, 2 Drawing Sheets

(56) References Cited

U.S. PATENT DOCUMENTS

| | | | |
|---|---|---|---|
| 8,670,521 | B2 | 3/2014 | Bothorel |
| 2005/0031086 | A1 | 2/2005 | Dalpiaz et al. |
| 2013/0071809 | A1 | 3/2013 | Kirkpatrick et al. |
| 2013/0162645 | A1 | 6/2013 | Ulrici |
| 2014/0010349 | A1 | 1/2014 | De Godzinsky et al. |
| 2014/0086389 | A1 | 3/2014 | Baek |
| 2015/0250435 | A1 | 9/2015 | Hyde |
| 2016/0038105 | A1 | 2/2016 | Hayman |
| 2020/0352530 | A1 | 11/2020 | Inglese et al. |

FOREIGN PATENT DOCUMENTS

| | | | |
|---|---|---|---|
| CN | 107708523 | | 2/2018 |
| CN | 111200970 | | 5/2020 |
| DE | 102017206321 | A1 | 10/2018 |
| EP | 2083697 | B1 | 5/2013 |
| EP | 3066984 | A2 | 9/2016 |
| EP | 2568882 | B1 | 9/2017 |
| EP | 3827751 | A1 | 6/2021 |
| EP | 3827751 | B1 | 6/2022 |
| JP | 2014508619 | A | 4/2014 |
| JP | 2016193163 | A | 11/2016 |
| JP | 2018518213 | A | 7/2018 |
| JP | 2018148993 | A * | 9/2018 |
| JP | 2018536487 | A | 12/2018 |
| JP | 2019521725 | A | 8/2019 |
| KR | 20200060717 | | 6/2020 |
| WO | 2007149402 | A2 | 12/2007 |
| WO | 2010098498 | A1 | 9/2010 |
| WO | 2010140492 | A1 | 12/2010 |
| WO | 2011141763 | A1 | 11/2011 |
| WO | WO-2019040056 | A1 * | 2/2019 |
| WO | WO-2021105397 | A1 | 6/2021 |

OTHER PUBLICATIONS

"European Application Serial No. 19212176.2, Partial European Search Report mailed May 19, 2020", 10 pgs.

"European Application Serial No. 19212176.2, Response filed Dec. 2, 2021 to Extended European Search Report mailed Aug. 10, 2020", 37 pgs.

"International Application Serial No. PCT/EP2020/083691, International Preliminary Report on Patentability mailed Jun. 9, 2022", 9 pgs.

"International Application Serial No. PCT/EP2020/083691, International Search Report mailed Feb. 3, 2021", 4 pgs.

"International Application Serial No. PCT/EP2020/083691, Written Opinion mailed Feb. 3, 2021", 7 pgs.

International Search Report; PCT/EP2020/083691; Jan. 22, 2021 (completed); Feb. 3, 2021 (mailed).

International Preliminary Report on Patentability; PCT/EP2020/083691; Jan. 22, 2021 (completed); Feb. 3, 2021 (mailed).

Written Opinion of the International Searching Authority; PCT/EP2020/083691; Jan. 22, 2021 (completed); Feb. 3, 2021 (mailed).

Lee et al; "Monitoring of typodont root movement via crown superimposition of single cone-beam computed tomography and consecutive intraoral scans"; American Journal of Orthodontics & Dentofacial Orthopedics; vol. 145, No. 3; Mar. 1, 2014; pp. 399-409.

Shumei Murakami; Virtual Endoscopy of Tooth Root by Dental CBCT Data; Manufacturing & Technology (Quarterly Magazine) 2012; vol. 64, No. 1; pp. 80-83; URL:http://seisan.server-shared.com/64-1-pdf.html.

Japanese Office Action dated Jun. 25, 2024.

"Canadian Application Serial No. 3156129, Examiners Rule 86(2) Report mailed Jun. 16, 2025", 4 pgs.

"Chinese Application Serial No. 202080082315.9, Response filed May 19, 2025 to Office Action mailed Jan. 18, 2025", W/English Claims, 20 pgs.

"Japanese Application Serial No. 6589.082JP1, Notification of Reasons for Refusal mailed Oct. 8, 2024", w English Translation, 6 pgs.

"Japanese Application Serial No. 2022-526189, Examiners Decision of Final Refusal mailed Sep. 27, 2024", W English Translation, 6 pgs.

"Japanese Application Serial No. 2022-526189, Response filed Feb. 7, 2025 to Examiners Decision of Final Refusal mailed Sep. 27, 2024", w current English claims, 8 pgs.

"Chinese Application Serial No. 202080082315.9, Office Action mailed Jan. 18, 2025", w English Translation, 17 pgs.

Lee, Robert J., "Monitoring of typodont root movement via crown superimposition of single cone-beam computed tomography and consecutive intraoral scans", American Journal of Orthodontics and Dentofacial Orthopedics. vol. 145. No. 3, (Mar. 1, 2014), 11 pgs.

"Japanese Application Serial No. 2022-526189, Notification of Reasons for Refusal mailed Jun. 25, 2024", w English Translation, 12 pgs.

"Chinese Application Serial No. 202080082315.9, Office Action mailed Aug. 16, 2025", w English Translation, 8 pgs.

\* cited by examiner

SENSOR HOLDER AND METHOD FOR OPTIMUM POSITIONING DURING INTRAORAL IMAGING

CROSS-REFERENCE TO RELATED APPLICATIONS

This is a National Phase application of International Application No. PCT/EP2020/083691, filed Nov. 27, 2020, which claims the benefit of and priority to European Application Ser. No. 19212176.2, filed on Nov. 28, 2019, which are herein incorporated by reference for all purposes.

FIELD OF THE INVENTION

The present invention relates to a sensor holder for intraoral imaging, its use in a method for intraoral imaging, a method for determining an optimum positioning in intraoral imaging and a method for producing such imaging.

BACKGROUND OF THE INVENTION

Following endodontic treatment, an intraoral control scan is usually performed to verify that all root canals have been successfully treated. For this purpose, it is necessary to capture each root canal without overlap by other root canals. Due to the anatomical situation, however, it is often difficult to align the imaging device and the sensor (for example, detectors such as a film or a phosphor plate) at the correct angle, so that all root canals may be imaged without overlapping and with a single image.

Usually, one attempts to estimate the angle by means of a so-called eccentric X-ray, and thus avoid the problem of root canal overlapping. Alternatively, multiple images may be taken from different angles in order to capture each root canal at least once without overlapping. There are numerous variations in the prior art how the position of the imaging device and the sensor may be optimized or aligned relative to each other.

EP 3 066 984, EP 2 568 882, WO 2011/141763 and WO 2007/149402, for example, describe sensors and/or transmitters on the sensor and the imaging device in order to avoid the application of radiation that does not reach the sensor. In US 2014/0086389 or US 2016/0038105 the problem of additional irradiation is solved, for example, by means of diaphragms on the positioning units. EP 2 083 697 describes a sensor holder whose beam holder may be rotationally changed but without a reliable description of the corresponding angle through which it should rotate. US 2013/0162645 describes the projection of individual teeth from a 3D volume, without establishing a connection between the positioning of the imaging device and the sensor. U.S. Pat. No. 8,670,521 describes a tomosynthesis method in which different positions between the imaging device and the sensor are used to calculate a pseudo-3D representation. This results in the subsequent possibility of distinguishing the root canals, but requires more than a single image.

However, none of the above methods describes a reliable positioning of the sensor and the imaging device to ensure non-overlapping imaging of all root canals without having to make an undesirable number of images.

Therefore, it is the object of the present invention to provide a sensor holder and corresponding methods for intraoral imaging, which overcome the disadvantages of the prior art and provide a solution in which non-overlapping imaging, for example of the root canals, is made possible without increased radiation exposure.

SUMMARY OF THE INVENTION

The above mentioned objectives of the present invention have been achieved through the computer-implemented method as defined in claim 1. The dependent claims define further developments and preferred embodiments of the present invention.

According to a first aspect of the invention, the present invention provides a sensor holder for intraoral imaging, which comprises at least one biting device that is insertable into the mouth of a patient, at least one holding device that is at least indirectly in operative connection with the biting device for fixing at least one sensor, and at least one centering means for aligning at least one imaging device, wherein the centering means is at least indirectly operatively connected with the biting device via at least one centering means holding portion, further wherein the centering means holding portion is designed such that positioning of the holding device relative to the centering means with respect to angle and/or distance is continuously variable.

The sensor holder according to the invention thus makes it possible to achieve flexible adjustment to enable intraoral imaging in an optimum manner. The principle of the sensor holder according to the invention is that a radiation source (i.e. an imaging source of an imaging system) is located outside the mouth while a sensor positioned in the patient's mouth is placed behind the tooth in the beam path, wherein the beam of the radiation source hits the sensor and thus an image of the tooth or certain parts thereof may be obtained. The radiation source is thereby aligned with a centering means located outside of the mouth.

The parameters for the flexible adjustment of the sensor holder, i.e. the position of the holding device with respect to the centering means, are determined by a previously performed analysis method, in particular software-supported. Examples of such analysis methods are known to those skilled in the art. In one embodiment of the present invention, a digital volume tomography (DVT) image is evaluated or produced. With a DVT image, for example, the actual course of the root canals may be safely and reliably mapped. When a corresponding DVT image is available, a virtual sensor and a virtual imaging device, in particular an imaging source for an intraoral image, may be incorporated in a software program to allow imaging to be simulated from various angles by appropriate projection. Thus, it is possible, without additional exposure for the patient, to determine the optimum position of the imaging device or imaging source and sensor in order to achieve a representation which is for example free of overlapping of all root canals, in subsequent imaging. If, for example, the optimum angle between the imaging device and/or imaging source and sensor has been determined (manually or automatically), the sensor holder is adjusted (manually or automatically), so that the imaging device and the sensor are at this optimum angle to each other during intraoral imaging. Thus, only one imaging shot is required to obtain as far as possible an image free of overlapping.

In another embodiment, the parameters for the flexible adjustment of the sensor holder may also be determined by another analytical method, for example, but not limited to, 3D volume tomography, 2D X-ray projection imaging, 3D surface scanning with recognizable root canal inputs, and/or 2D imaging with recognizable root canal inputs.

It may be provided that the biting device is at least partially attached to the holding device, the centering means is connected to the biting device and/or to the centering means holding portion, and/or the centering-means holding portion comprises one or more movable elements selected from the group consisting of ball joint, swivel joint, tilting joint, turn-tilt mechanism and/or a combination thereof.

The flexible adjustment options of the sensor holder are so designed that the centering means holding portion comprises one or more movable elements. Movable elements in this context means that the centering means holding portion may be twisted, angled, extended and/or shortened at one or more points. In one embodiment of the invention, the one or more movable elements may be selected from the group consisting of, but not limited to, ball joint, swivel joint, tilting joint, turn-tilt mechanism and/or a combination thereof. In one embodiment of the present invention, the centering means holding portion has a ball joint. The movable elements may be adjusted continuously or may have a mechanism that leads to engagement at various gradations. In one embodiment, the movable elements may be continuously adjusted.

In order to adjust the exact positioning of the holding device for the centering means, the centering means holding portion according to the invention may include at an appropriate position, at least one display device, in particular comprising at least one scale, for adjusting the positioning of the holding device and the centering means holding portion. The display device, in particular a scale, may preferably be positioned directly on the one or more movable elements. With the aid of such a scale, the position of the holding device with respect to the centering means may be precisely adjusted, irrespective of what the mutual position should be, i.e. regardless of angle, distance or other parameters.

The display device and/or scale may be any type of display and/or scale that is capable of enabling exact positioning of the elements. For example, the display and/or scale may be selected from the group consisting of, but not limited to, a color scale, an angular indication, a letter scale, or a combination thereof. A display device and/or scale, which has an angular indication, is preferred. Depending on the embodiment, the scale may have scale units of different sizes, in particular for coarse and fine adjustment.

Depending on the design of the sensor holder according to the invention, the positioning of the holding device and the centering means may be carried out manually, semi-automatically and/or automatically.

In the case of manual positioning, the determined position data are transmitted to the sensor holder with the help of one or more scales via the one or more movable elements of the centering means holding device. In the case of automatic positioning, the determined position data are either transmitted by radio and applied to the sensor holder according to the invention, in particular by means of an actuator, or the position date are transmitted via a physical connection, for example a cable connection, to a data transmission device, e.g. a computer or a DVT imaging and/or analysis device. Possible radio transmissions may, for example, be carried out via Bluetooth, RFID, NFC and/or a combination thereof, but are not limited thereto.

In a further embodiment of the invention, the positioning of the holding device and the centering means may be performed both manually and automatically. For example, automatic presetting may be performed, followed by a manual fine adjustment or vice versa. In the case of automatic position adjustment, the sensor holder according to the invention has one or more actuators, preferably motors, which perform the position adjustment.

In one embodiment of the invention, the sensor holder may include, for example, at least one receiver selected from the group consisting of Bluetooth, RFID, NFC and/or a combination thereof and/or an LED which allows manual adjustment of the positioning.

In an alternative and/or supplementary embodiment of the invention, the sensor holder may comprise at least one actuator, preferably at least one motor, a receiver selected from the group consisting of Bluetooth, RFID, NFC and/or a combination thereof, and/or a scale which enables automatic positioning.

The sensor holder according to the invention may also comprise at least one triggering prevention facility for the imaging device, if a non-optimum positioning of the holding device is adjusted with respect to the centering means, or may cooperate with such a triggering prevention facility. A triggering prevention facility ensures that the imaging device may only be triggered when the optimum positioning of the holding device with respect to the centering means is set, i.e. when the set position data corresponds to the calculated position data. Embodiments of such a triggering prevention facility are known to those skilled in the art. For example, the sensor holder can prevent radio triggering of the imaging device if the determined positioning data does not match the position set on the sensor holder.

Additionally or alternatively, the sensor holder according to the invention may comprise at least one display unit, which preferably indicates when the positioning of the holding device is not optimally adjusted with respect to the centering means. Such a display unit may be configured in various ways. For example, the display may be provided via an external display that is connected to the sensor holder via radio or another suitable element. In other embodiments, the display may be provided via an audible or visual signal, or a combination thereof.

In a further embodiment of the invention, the display unit may be so designed so that instructions for a correct, in particular manual positioning of the sensor holder, are displayed.

Preferably, the centering means is configured in such a way that irradiation by the imaging device is substantially directed to an active and/or sensitive region of the sensor, in particular to an active and/or sensitive sensor surface of the sensor, and/or preferably radiation of the imaging device is at least partially stopped or attenuated by the centering means. According to the required imaging, in one embodiment, the centering means and/or the sensor may be exchanged in order to achieve an optimum result.

The sensor that may be used in the sensor holder of the present invention is an element that can provide an image of the desired area of the mouth. In one embodiment of the present invention, the sensor is selected from the group consisting of at least one X-ray film, at least one storage film and at least one digital image sensor. In a preferred embodiment, the sensor is a storage film or digital X-ray sensor.

The holding device for fixing the sensor may be in the form, for example, of a molded part, which comprises two clamping arms, which can hold and fix an inserted sensor. This allows the sensor to be easily inserted and safely retained in position. In another embodiment, the holding device may be replaced so that the most suitable sensor may be used for imaging.

In a second aspect, the invention is directed to the use of the sensor holder according to the invention in a method for intraoral imaging. In this case, the sensor holder is positioned in the corresponding position in the patient's mouth, then the holding device is aligned with the centering means in accordance with the determined position data and the acquisition is carried out.

In a further aspect, the invention is directed to a method for determining an optimum, in particular relative, position of at least one sensor and/or at least one imaging source of at least one imaging device for at least one intraoral imaging, in particular for non-overlapping imaging of at least two tooth root canals, wherein the method comprises a) the evaluation of at least one digital image of a patient; and b) the determination of the optimum position of the sensor and the imaging source based on the evaluation mentioned under a).

The digital imaging may be, for example, but not limited to, digital volume tomography (DVT) imaging, 3D volume tomography, at least two 2D X-ray projection images, 3D surface scans with recognizable root canal inputs, or 2D imaging with detectable root canal inputs.

The evaluation of the data obtained may be carried out in different ways, for example by the simulation of a sensor, an imaging source and/or angles and/or positions, by ray-tracing or by collision detection of previously marked root canals.

For example, it is preferable that evaluation of an image, in particular a DVT image, preferably comprises the simulation of a projection of at least one virtual sensor and/or at least one virtual imaging source from at least two different angles and/or positions for the imaging, of the intraoral anatomy of the patient.

It is also proposed that, for example, the simulation should be carried out several times, wherein preferably the optimum angle and/or the optimum position is determined iteratively so that overlapping of the root canals is minimized, preferably avoided.

In the two aforementioned embodiments, it is preferred that the intraoral anatomy comprises the position and/or aligning of at least two teeth, at least two root canals, and/or at least one area of the soft tissue of the patient.

Furthermore, the invention provides a method for producing at least one intraoral imaging of at least one patient, comprising carrying out a method according to the invention for determining the optimum position of a sensor and an imaging source.

In this case, the invention also proposes that the method comprises manual, semi-automatic and/or automatic adjustment, preferably by means of at least one actuator, wherein the optimum position and/or the optimum angle of the sensor and/or the imaging source is, in particular, relative to at least one predetermined position of the patient, preferably by means of at least one sensor holder according to the invention.

In the aforementioned two embodiments, it is preferred that the method comprises the production of at least one intraoral imaging after setting the optimum position of the sensor and/or the imaging source.

Finally, it is proposed for this method that the imaging source is at least partially formed by an X-ray device and/or comprises at least one X-ray device.

Furthermore, the invention provides a computer-implemented method for carrying out a method according to the invention.

The invention is also directed to an apparatus for data processing, comprising at least one processor that is adapted to the steps of the inventive method for determining the optimum position of a sensor and/or an imaging source and/or the inventive method for producing at least one intraoral image, as well as a computer program product comprising instructions which, when the program is executed by a computer, in particular a data processing unit according to the invention, executes the steps of the method according to the invention for determining the optimum position of a sensor and/or an imaging source and/or the method according to the invention for producing at least one intraoral image and a computer-readable storage medium comprising instructions for execution by a computer, in particular a device according to the invention for data processing, causing the latter to carry out the steps of the method according to the invention for determining the optimum position of a sensor and/or an imaging source and/or the method according to the invention for producing at least one intraoral image.

The digital volume tomography imaging is performed according to the usual specifications. As already explained above, a virtual sensor and a virtual imaging device for an intraoral image are positioned in a simulation using, for example, the data of a DVT image in a computer. Then, a projection from different angles may be simulated by appropriate projection in order to determine the optimum position of both the sensor and the imaging source. The thus determined position data are transmitted manually, semi-automatically and/or automatically to the imaging system, in particular the sensor holder according to the invention, or adjusted there. After positioning the correspondingly adjusted sensor holder, the actual imaging is carried out.

In one embodiment, the imaging source is preferably an X-ray device.

The above-listed embodiments may be used individually or in any combination with one another for the design of the device according to the invention and of the method according to the invention.

BRIEF DESCRIPTION OF THE FIGURES

Further features and advantages of the invention will be described in the following description, preferred embodiments of the invention being explained by reference to the following drawing.

FIG. 4a shows the result of a virtual projection from a first position; while

DETAILED DESCRIPTION OF THE INVENTION

Figure 1:
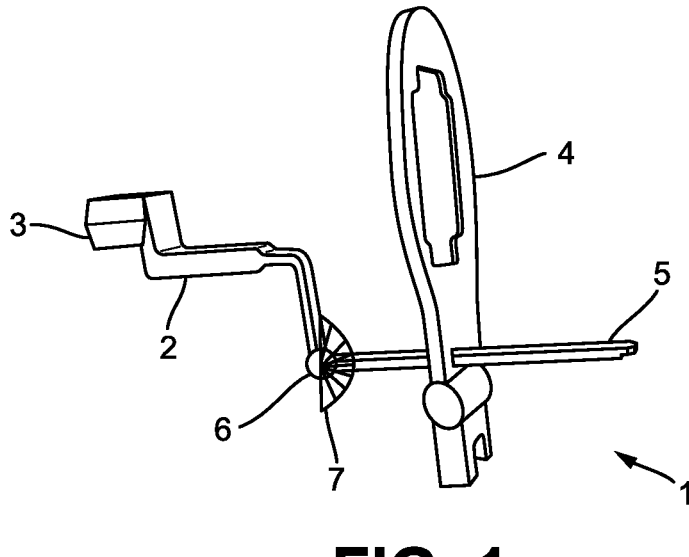
FIG. 1 shows an embodiment of a sensor holder according to the invention.

According to a first embodiment of the present invention, FIG. 1 shows a sensor holder (1) according to the invention with a biting device (2) on which a holding device (3) for the sensor (not shown) is provided. This part of the sensor holder (1), after a corresponding sensor has been inserted into the holding device (3), is inserted into the mouth of the patient, wherein the patient holds the sensor holder (1) in place by biting on the biting device (2). In this case, the positioning of the holding device (3) and the centering means (4) may be adjusted before insertion into the mouth or even after the sensor holder (1) is positioned in the mouth of the patient and held by the latter. The centering means holding portion (5), which passes out of the patient's mouth and is connected to the biting device (2) in the embodiment according to FIG. 1, has a ball joint (6) with a display device in the form of a scale (7), by means of which the desired position data may be set. For this purpose, the ball joint 6 includes an actuator (not shown) that is at least in operative connection, wherein data are received from a non-illustrated radio receiver for controlling the actuator of the sensor holder 1. At the other end of the centering means holding portion (5) is the centering means (4), which serves to position the imaging device, in particular an imaging source of the imaging device (not shown). In this case, the imaging device or the imaging source is so positioned that the corresponding radiation is at right angles to the opening in the centering means (4) and is therefore also at right angles to the sensor located in the mouth.

The implementation of a method according to the invention is illustrated below with reference to FIGS. 2 to 4b.

Figure 2:
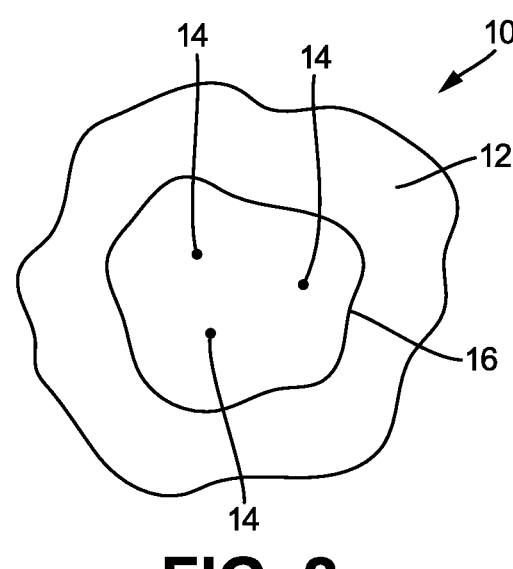
FIG. 2 shows schematically a surface scan of a tooth.

FIG. 2 schematically shows a digital image, in particular of a tooth in a plan view. The image is a 2D or surface scan, but one may also use 3D DVT imaging. As may be seen from FIG. 2, a tooth 10 has a tooth body 12 as well as root canals 14 and an opening 16.

Figure 3:
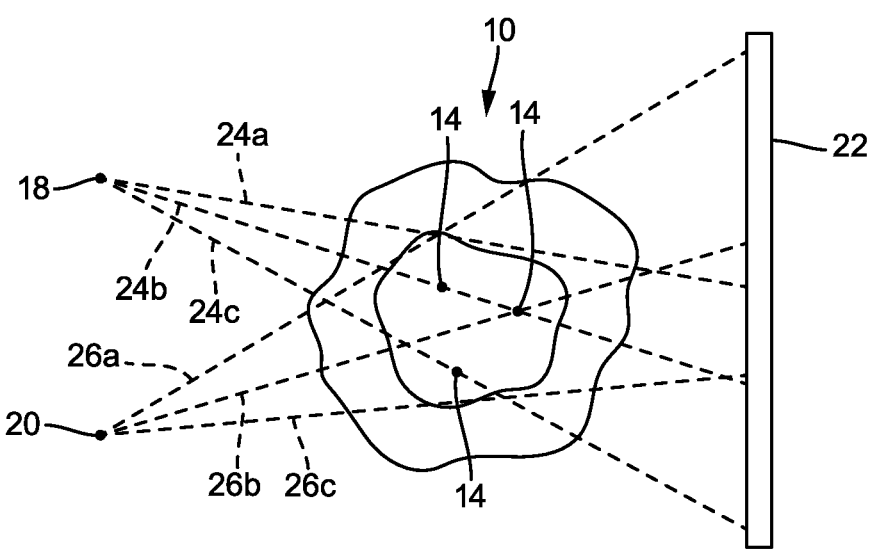
FIG. 3 shows schematically the beam path for 2 positions of an imaging device when receiving a tooth.

FIG. 3 shows schematically the beam path for two positions 18, 20 of a radiation source of an imaging device relative to a sensor 22 of the imaging device with respect to the tooth 10. So-called ray-tracing or collision detection will be explained below with reference to FIG. 3. When the radiation source is positioned relative to the sensor 22 at position 18, the rays are incident on the sensor 22 after passing through the tooth 10, as exemplified by beams 24a and 24b and 24c. As the beam 24a passes through a portion of the tooth 10 in which no root canal 14 is present, the beam 24c passes through a root canal 24 and thus reflects it to the sensor 22. However, it is problematic at the position 18 that the beam 24b passes through two root canals 14 in such a way that they mutually shadow each other or cannot be resolved on the sensor 22, in particular an active sensor surface.

If, on the other hand, the radiation source is arranged at the position 20 relative to the sensor 22, the profiles shown by way of example with reference to the beams 26a, 26b and 26c result. As may be seen from FIG. 3, the rays emanating from the position 20 pass onto the sensor 22 after passing through the tooth 10 so that the respective individual rays only pass through one root canal 14 in each case. By way of example, the beam 26b is shown passing through a root canal 14.

Corresponding beams between the beams 26a and 26b and the beams 26b and 26c, respectively, pass through the two further root canals 14 without these being mutually shadowed or overlapping.

The aim of the method according to the invention is now to produce a relative arrangement of the imaging device, in particular the radiation source and/or the sensor, with respect to the tooth 10 in such a way that shadowing of the root canals is avoided. For example, the radiation source and the sensor are so arranged that the beam path corresponds to the arrangement of the radiation source at position 20 in FIG. 3.

Figure 4A:
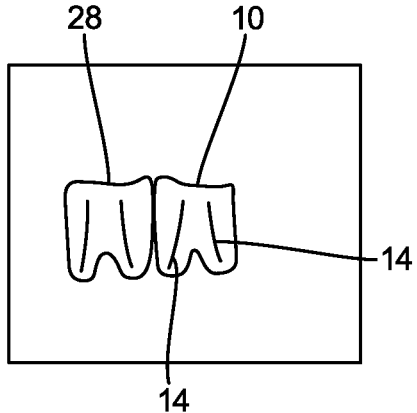
Figure 4B:
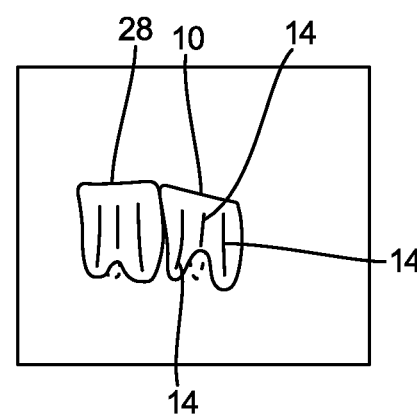
FIG. 4b shows the result of a virtual projection from a second position.

The inventive method simulates the positioning of the radiation source or of the sensor at different positions based on the image information of the image shown in FIG. 2. The images shown in FIGS. 4a and 4b are generated by means of the simulation. The illustration shown in FIG. 4a corresponds to the simulation of the beam path when the radiation source is arranged at position 18 in FIG. 3, while FIG. 4b represents the result of the simulation of the beam path when the radiation source is arranged at position 20.

As may be seen from FIG. 4a, in which the tooth 10 is shown together with an adjacent tooth 28, which was not shown in FIG. 2 for the sake of simplicity, the positioning of the radiation source at the position 18 results in only two root canals 14 of the tooth 10 being seen due to the mutual shadowing. If, on the other hand, the positioning of the beam path is simulated, the image shown in FIG. 4b results when the radiation source is arranged at position 20. In this simulation, it may be seen that all three root canals 14 of the tooth 10 may be imaged without mutual shadowing.

According to the method of the invention, such a relative positioning of the sensor is set with respect to a radiation source of the imaging apparatus by means of the sensor holder to result in the beam path indicated by the beams 26a to 26c.

The embodiments shown here are only an example of the present invention and should not be understood as limiting. Alternative embodiments contemplated by those skilled in the art are equally within the scope of the present invention, and in particular, the features disclosed in the specification, claims, and figures, both individually and in any combination, may be material to the invention in the various embodiments.

LIST OF REFERENCE NUMBERS 1 sensor holder
2 biting device
3 holding device
4 centering means
5 centering means holding portion
6 movable element
7 scale
10 tooth
12 tooth body
14 root canal
16 opening
18 position
20 position
22 sensor
24a, 24b, 24c beam
26a, 26b, 26c beam
28 tooth

The invention claimed is:

1. A computer-implemented method for determining the optimum relative position of at least one sensor or at least one imaging source of an imaging device for at least one intraoral imaging, and for the non-overlapping imaging of at least two tooth root canals, the method comprises:

a) evaluating at least one digital image of a patient;

b) computing an optimum position of the sensor and the imaging source based on the evaluation mentioned under a); and c) manually, semi-automatically or automatically adjusting, by at least one actuator, the optimum position or the optimum angle of the sensor or the imaging source, relative to at least one predetermined position of the patient, by at least one sensor holder, wherein the evaluating comprises an evaluation of a digital recording, namely a volumetric tomography (DVT) imaging, which comprises the simulation of a projection of at least one virtual sensor or at least one virtual imaging source from at least two different angles or positions for the imaging, or DVT imaging of the intraoral anatomy of the patient, wherein, the simulation is carried out several times, and wherein an optimum angle or the optimum position is computed so that overlapping of the root canals is minimized, and largely avoided, and wherein, to enable automatic positioning, for receiving or for displaying the positioning enabling data, the sensor holder is provided with at least one actuator, at least one motor receiver selected from the group consisting of Bluetooth, RFID, NFC or a combination thereof, or a scale, of the sensor holder.

2. The method according to claim 1, wherein the intraoral anatomy comprises at least one position or aligning of at least two teeth, at least two root canals, at least one area of the soft tissue of the patient.

3. The method according to claim 1, wherein at least one intraoral imaging of at least one patient is generated.

4. The method according to claim 3, wherein, at least one intraoral imaging is produced after adjustment of the optimum position of the sensor or the imaging source.

5. The method according to claim 4, wherein a positioning of a holding device of the sensor holder and a centering means holding portion is carried out manually, semi-automatically or automatically, and wherein for enabling a manual adjustment of the positioning, for receiving or displaying data supporting the positioning, the sensor holder is provided with at least one receiver selected from the group consisting of Bluetooth, RFID, NFC or a combination of these, or the scale.

6. The method according to claim 4, wherein irradiation by the imaging device is directed to an active or sensitive sensor surface of the sensor, wherein radiation of the imaging device is at least partially stopped or attenuated by a centering means.

7. A data processing unit comprising at least one processor configured to perform the steps of the method according to claim 1.

8. Computer program comprising instructions which when executed a data processing unit causes the data processing unit to perform the steps according to claim 1.

9. A non-transitory computer readable media storing instructions which when executed by a computer system causes the computer system to perform the steps of claim 1.

* * * * *